US012805711B2

(12) United States Patent
Pathak et al.

(10) Patent No.: US 12,805,711 B2
(45) Date of Patent: Nov. 24, 2026

(54) MEDICAL INSTRUMENTATION UTILIZING NARROWBAND IMAGING

(71) Applicant: NSV, Inc., Allentown, PA (US)

(72) Inventors: Soham Pathak, Allentown, PA (US); Ankita Shastri, Bothell, WA (US); Bipin D. Dama, Bridgewater, NJ (US); Kalpendu Shastri, Orefield, PA (US); Rao Yelamarty, Allentown, PA (US)

(73) Assignee: NSV, Inc., Allentown, PA (US)

( * ) Notice: Subject to any disclaimer, the term of this patent is extended or adjusted under 35 U.S.C. 154(b) by 97 days.

(21) Appl. No.: 17/441,839

(22) PCT Filed: Apr. 3, 2020

(86) PCT No.: PCT/US2020/026589
§ 371 (c)(1),
(2) Date: Sep. 22, 2021

(87) PCT Pub. No.: WO2020/206261
PCT Pub. Date: Oct. 8, 2020

(65) Prior Publication Data

US 2022/0183544 A1 Jun. 16, 2022

Related U.S. Application Data

(60) Provisional application No. 62/829,078, filed on Apr. 4, 2019.

(51) Int. Cl.
*A61B 1/06* (2006.01)
*A61B 1/00* (2006.01)
(Continued)

(52) U.S. Cl.
CPC ........ *A61B 1/0684* (2013.01); *A61B 1/00186* (2013.01); *A61B 1/04* (2013.01);
(Continued)

(58) Field of Classification Search
CPC ..... A61B 1/0684; A61B 1/00186; A61B 1/04; A61B 1/0638; A61B 1/303; A61B 5/0071; A61B 5/441
See application file for complete search history.

(56) References Cited

U.S. PATENT DOCUMENTS 8,224,427 B2 7/2012 Kopriva
8,289,378 B2 10/2012 Soto-Thompson et al.
(Continued)

OTHER PUBLICATIONS

Hsiao et al., "Identified early stage mycosis fungoides from psoriasis and atopic dermatitis using non-invasive color contrast enhancement by LEDs lighting", Optical and Quantum Electronics, Springer US,, vol. 47, No. 7, (Sep. 17, 2014), p. 1599-1611, (Year: 2014).*
(Continued)

*Primary Examiner* — Joseph L Williams
*Assistant Examiner* — Michael Chiang
(74) *Attorney, Agent, or Firm* — Studebaker Brackett PLLC

(57) ABSTRACT

An illumination source comprised of individual light emitting diodes (LEDs) specifically formed to operate at wavelengths associated with the absorption spectrum of certain biomolecule(s) of interest present in the region of the body being examined. Advantageously, LEDs may be configured to generate a high intensity, narrowband beam that is well-suited for these medical imaging purposes where the ability to provide a proper diagnosis relies on the ability to create a high contrast image for review by the medical professionals. The inventive illumination source may also include a conventional white light source that is used as before for general observation purposes, with the one or more narrowband LEDs activated when there is a need to create a high contrast image of a particular ROI.

17 Claims, 4 Drawing Sheets

(51) Int. Cl.
*A61B 1/04* (2006.01)
*A61B 1/303* (2006.01)
*A61B 5/00* (2006.01)

(52) U.S. Cl.
CPC ............ *A61B 1/0638* (2013.01); *A61B 1/303* (2013.01); *A61B 5/0071* (2013.01); *A61B 5/441* (2013.01)

(56) References Cited

U.S. PATENT DOCUMENTS

| | | | | |
|---|---|---|---|---|
| 9,561,003 | B2 | 2/2017 | Bambot et al. | |
| 10,028,649 | B2 | 7/2018 | Salvati et al. | |
| 10,491,789 | B2 | 11/2019 | Shen et al. | |
| 11,399,706 | B2 | 8/2022 | Ito et al. | |
| 2004/0111031 | A1 | 6/2004 | Alfano et al. | |
| 2005/0280813 | A1 | 12/2005 | Jones et al. | |
| 2006/0215406 | A1 | 9/2006 | Thrailkill | |
| 2009/0034824 | A1 | 2/2009 | Li et al. | |
| 2009/0082695 | A1 | 3/2009 | Whitehead | |
| 2009/0306478 | A1* | 12/2009 | Mizuyoshi | A61B 1/07 600/478 |
| 2014/0364691 | A1* | 12/2014 | Krivopisk | A61B 1/05 600/165 |
| 2015/0185151 | A1 | 7/2015 | Utzinger et al. | |
| 2015/0231407 | A1 | 8/2015 | Klem et al. | |
| 2016/0227994 | A1 | 8/2016 | Gotsch et al. | |
| 2016/0287061 | A1* | 10/2016 | Shigeta | A61B 1/0005 |
| 2016/0287063 | A1* | 10/2016 | Ramanujam | A61B 1/00087 |
| 2017/0014022 | A1 | 1/2017 | Tamura et al. | |
| 2017/0127914 | A1* | 5/2017 | Salman | A61B 1/126 |
| 2017/0272720 | A1* | 9/2017 | Oki | A61B 1/0655 |
| 2019/0117055 | A1* | 4/2019 | Ito | G02B 23/2461 |
| 2019/0216325 | A1* | 7/2019 | Ouyang | A61B 1/00096 |
| 2021/0161372 | A1* | 6/2021 | Iwane | A61B 1/000094 |

OTHER PUBLICATIONS

Silva, Manuel, et al., "NBI Optical Filters in Minimally Invasive Medical Devices", IEEE Journal of Selected Topics in Quantum Electronics, IEEE, USA, vol. 22 No. 4, Jul./Aug. 2016, pp. 1-7.

Hsiao, Yu-Ping, et al., "Identified Early Stage Mycosis Fungoides from Psoriasis and Atopic Dermatitis using Non-Invasive Color Contrast Enhancements by LEDs Lighting", Optical and Quantum Electronics, Springer US, New York, vol. 47, No. 7, Sep. 17, 2014, pp. 1599-1611.

Roblyer, Darren, et al., "Multispectral Optical Imaging Device for In Vivo Detection of Oral Neoplasia", SPIE, Journal of Biomedical Optics, Mar./Apr. 2008, vol. 13(2), pp. 024019-1 to 024019-11.

Clancy, Neil T., et al., "Development and Evaluation of a Light Emitting Diode Endoscopic Light Source", Advanced Biomedical and Clinical Diagnostic Systems, SPIE, vol. 8214, No. 1, Mar. 8, 2012, pp. 1-7.

Venkataraman, Sankar et al. "Improving Cervical Region of Interest by Eliminating Vaginal Walls and Cotton-Swabs for Automated Image Analysis", Proc of SPIE, vol. 6914, 69143E (2008), pp. 1-8.

* cited by examiner

MEDICAL INSTRUMENTATION UTILIZING NARROWBAND IMAGING

CROSS-REFERENCE TO RELATED APPLICATIONS

This application claims the benefit of U.S. Provisional Application No. 62/829,078, filed Apr. 4, 2019, and herein incorporated by reference.

TECHNICAL FIELD

The present invention relates to improving medical instrumentation that utilizes visual imaging of a region of interest and, more particularly, to the utilization of narrowband light sources emitting at specific, predefined wavelengths to enable the viewing (and capture) of high contrast digital images without the use of filtered white light.

BACKGROUND OF THE INVENTION

There are several types of medical procedures that utilize image analysis of selected specimens to aid in the development of a proper diagnosis. Dermatoscopy, for example, may utilize an analysis of lesion texture and topology, or specific pigmentation characteristics associated with melanocytes in determining a diagnosis. Colposcopy is known to extensively utilize analysis of vascular systems in evaluating a patient's condition. These are but two specific areas of the use of imaging analysis in the field of medicine.

Dermatoscopes include a magnifying optical system, a light source illuminating the region to be examined (with hopefully as few reflections as possible), and a power supply for providing electrical energy to the light source. During a medical examination, the dermatoscope is normally placed with a contact plate made of glass on the skin, which is then observed through the optical system. In certain embodiments, dermatoscopic oil or another liquid having a glass-like refractive index is placed between the skin and the dermatoscope, or the contact plate. Some embodiments make use of polarized illumination, since some medical diagnoses are only possible if the region to be examiner is viewed under specialized lighting configurations.

An optical colposcope comprises a binocular microscope with a built-in white light source and objective lens attached to a support mechanism. Various levels of magnification are often necessary to detect and identify certain vascular patterns indicative of the presence of more advanced pre-cancerous or cancerous lesions. During a colposcopic exam, acetic acid and iodine solutions are usually applied to the surface of the cervix to improve the visualization of abnormal areas. In colposcopy, abnormality of cervical tissue is often assessed with what is known as the “Swede score”. This score specifically takes into account crucial characteristics of cervical tissue such as vessel patterns, which can be assessed and deemed to fall into one of three categories: (1) “fine and regular”; (2) “absent”; or (3) “course or atypical”. In some cases, different-colored filters are used to accentuate blood vessel patterns that cannot be easily seen by using regular white light. This type of vasculature imaging is also useful when viewing oral mucosa and submucosa for the presence of premalignant lesions associated with various oral cancers.

However, since there is no standard wavelength or spectral bandwidth defined for these filters, different clinical settings may apply “green filters” that transmit so-called green light at different wavelengths, perhaps with different bandwidths. The use of such filters can produce less effective images in some cases, or lead to less consensus between different images of differing qualities. Additionally, green filters placed over white light inevitably diminish the transmission of light, and captured images often appear darker than they should.

In recent times, advances in digital imaging and various software/algorithmic techniques related to imaging have improved the quality of the images in these endeavors and reduced the need to use polarized light or certain filters to capture images. While considered an advance in the state-of-the-art, these techniques are applied subsequent to the process of creating and storing the images. A need remains to improve the quality, resolution, and detail of the images created in the first instance.

SUMMARY OF THE INVENTION

The need remaining in the prior art is addressed by the present invention, which relates to digital imaging for vasculature analysis and, more particularly, to the utilization of light sources emitting at specific, predefined wavelengths to enable narrowband digital imaging without the use of filters.

In accordance with the present invention, it is proposed to eliminate the use of color-based filters and, instead, provide an illumination source comprised of individual light emitting diodes (LEDs) specifically formed to operate at the wavelengths of interest (e.g., “green”, “blue”, “red”, “yellow”, etc.) based on the absorption spectrum of certain biomolecule(s) of interest present in the region of the body being examined. Advantageously, LEDs may be configured to generate a high intensity, narrowband beam that is well-suited for these medical imaging purposes where the ability to provide a proper diagnosis relies on the ability to create a high contrast image for review by the medical professionals.

In one exemplary embodiment, the present invention takes the form of an illumination source useful in performing digital imaging in conjunction with medical scopic instrumentation. The illumination source comprises at least one narrowband LED operating at a first center wavelength $\lambda_1$ associated with a first absorbance peak of a biomolecule present in an anatomical region of interest (ROI) under study, and perhaps another narrowband LED operating at a second center wavelength $\lambda_2$ associated with a second absorbance peak of either the same or a different biomolecule(s) present in the anatomical region of interest (ROI) under study (if the biomolecule in the ROI has two separate absorbance peaks, for example, hemoglobin). The LEDs are controlled in a manner that enhances the contrast between a specific set of features in the ROI and surrounding material, enabling the generation of a high-contrast digital image of the ROI.

The inventive illumination source may also include a conventional white light source that is used as before for general observation purposes, with the one or more narrowband LEDs activated when there is a need to create a high contrast image of a particular ROI. The turning “on” and “off” of the narrowband LEDs may be controlled by the individual performing the examination, with LED(s) at the first wavelength energized at a specific time when there is a need to capture a high contrast image (and other LED(s)) perhaps energized at another point in time during the examination. The captured high contrast images may be digitized and stored for analysis at a later point in time, by an individual at a remote location, or the like.

Other and further embodiments and features of the present invention will become apparent during the course of the following discussion and by reference to the accompanying drawings.

BRIEF DESCRIPTION OF THE DRAWINGS

Referring now to the drawings, where like element include like reference numbers in several views.

DETAILED DESCRIPTION

As mentioned above, clear, high-contrast images of selected specimens are vital for diagnostic impressions, particularly when performing pre-cancer and cancer screening. In accordance with the principles of the present invention, it is proposed to use narrowband light sources, operating at specific pre-determined wavelengths, to produce extremely high contrast images of the portion of the anatomy under study (that is, the "region of interest" or ROI).

Figure 1:
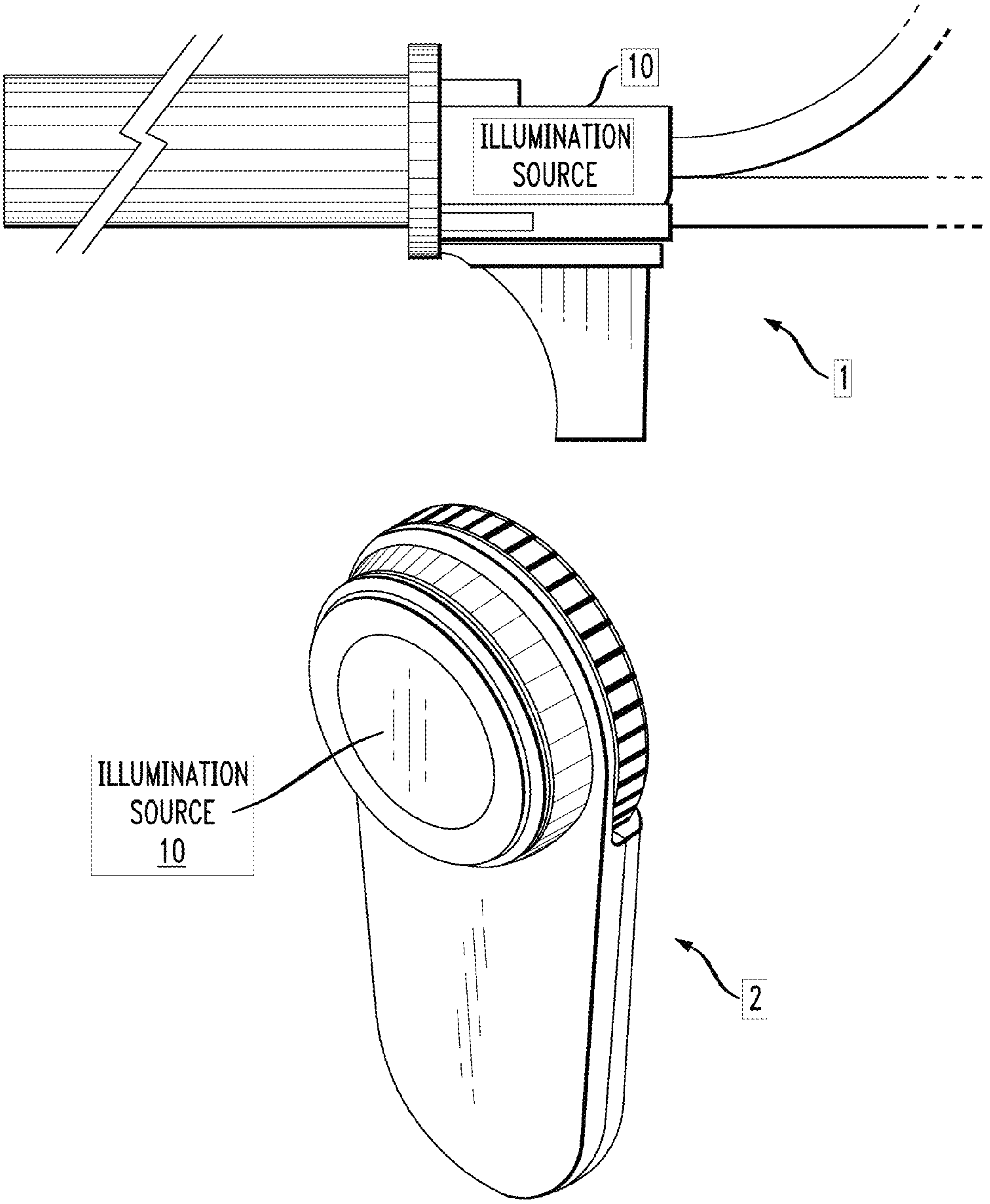
FIG. 1 depicts examples of medical instrumentation used to perform optical imaging.

FIG. 1 illustrates exemplary types of medical instrumentation that are used to perform optical imaging and include an illumination source that may be formed to include the LED-based system of the present invention. In particular, FIG. 1 depicts a side view of an exemplary colposcope 1, used in the examination of the cervix (e.g., to study the vasculature system of the cervix). While the specific instrument shown in FIG. 1 is rather compact (and thus portable), many colposcopy systems are large combinations of elements situated in an examination room. An exemplary dermatoscope 2 is also shown in FIG. 1. This type of medical instrumentation is used to view the skin (often with some type of oil or lotion applied to the surface of the skin before bringing the dermatoscope in contact.

Medical instrumentation such as that shown in FIG. 1 is typically based upon the use of a "white light" (full visible spectrum) source to aid the medical professional performing the examination to clearly see the "region of interest" (referred to hereinafter as the "ROI"). It has been known for years, however, that light at certain wavelengths can assist in improving the visualization of blood vessels, skin pigments, mucous, and the like. For example, imaging the cervix with "green" or "blue" light has been found to produce higher contrast images of the underlying vasculature than illumination with white light, since the absorbance spectrum of hemoglobin (a major component of the vessels) includes peaks in the visible part of the spectrum at wavelengths of about 415 nm ("blue" filtered light) and about 540 nm ("green" filtered light). Similar green/blue filters are also used in the study of oral mucosa and submucosa for the presence of premalignant lesions. Abnormal lesions or melanocytes on the surface of the skin (or in the tissue layers immediately beneath the surface) may be better distinguished by using "red" filtered light (a wavelength of about 625 nm) or "yellow" filtered light (a wavelength of about 580 nm).

In the prior art, the medical imaging apparatus utilized various "color" filters in combination with the standard white light source to alter the color of the ROI. As mentioned above, since there is no standard wavelength or spectral bandwidth defined for these filters, different clinical settings may apply "green" filters (using "green" as just one example) that transmit so-called green light at different wavelengths, perhaps with different bandwidths. Moreover, many of these filters may be wideband devices (e.g., bandwidths over 50 nm) that are too broad in spectral response to create an image that clearly delineates boundaries between normal and abnormal tissue. As a result, the use of such filters may produce less effective images in some cases, or lead to less consensus between different images of differing qualities. Additionally, the utilization of these filters in combination with a white light source inevitably diminishes the intensity of the transmitted beam, and captured images often appear darker than they should.

In accordance with the principles of the present invention, it is proposed to eliminate the use of such color-based filters and, instead, provide an illumination source comprised of individual light emitting diodes (LEDs) specifically formed to operate at the wavelengths of interest (e.g., "green", "blue", "red", "yellow", etc.). Advantageously, LEDs may be configured to generate a high intensity, narrowband beam that is well-suited for these medical imaging purposes where the ability to provide a proper diagnosis relies on the ability to create a high contrast image for review by the medical professionals.

When used as an illumination source for a colposcope, the inventive LED-based source utilizes one or more LEDs that emit at specifically-defined wavelengths that are referenced as "green" and "blue". The green and blue wavelengths emitted by the LEDs is absorbed by the vessels, while being reflected by the surrounding tissue that lacks hemoglobin. This increases the contrast with which vessels appear in the image. The narrower the bandwidth of the blue and green light (i.e., bandwidths on the order of about 30 nm, or perhaps less) around hemoglobin's absorbance peaks, the greater is the contrast of the vessels in the resulting image. The high contrast between the tissues and vessels significantly improves the visualization of blood vessel patterns, where certain patterns are a known indicator of tissue abnormality. Therefore, the ability to create (and thereafter store) digital images with this level of clarity is a vital need for diagnostic impressions of pre-cancer and cancer (for studying oral mucosa and submucosa as well).

As will also be discussed below, inasmuch as the two different wavelengths penetrate to a different depth within the ROI, by controlling the sequence of illumination for these LEDs (e.g., a "green" exposure, followed by a "blue" exposure), variations in the vasculature at different levels within the tissue may be discerned, providing a "three-dimensional" imaging result.

When used as an illumination source for a dermatoscope, the wavelengths for "red" and "yellow" light beams are known to coincide with the absorbance peaks of medically-relevant pigments (e.g., melanocytes).

In accordance with the principles of the present invention, the number of separate LEDs used, as well as their relative placement within the illumination source, provides the ability to individually manipulate the brightness of the narrowband illumination such that high quality, high contrast images are captured with sufficient brightness and clarity.

In a specific embodiment of the present invention, a scopic diagnostic tool is utilized to illuminate a particular ROI with a collection of illumination sources operating at specific, well-defined wavelengths. In many cases, a first set of LEDs (all operating at a first defined wavelength $\lambda_1$) and a second set of LEDs (all operating at a second defined wavelength $\lambda_2$) are used as part of the imaging system for these scopes. The LEDs are particularly selected to exhibit a narrow bandwidth to produce a high contrast result, particularly to aid in delineating the boundary between normal and abnormal areas within the ROI. For example, LEDs operating at a "green" wavelength of $\lambda_1 \approx 540$ nm that exhibit a full-width-half-maximum (FWHM) of 30 nm, and LEDs operating at a "blue" wavelength of $\lambda_2 \approx 415$ nm that exhibit a FWHM of 12 nm can be used, where the FWHM is a well-understood figure of merit defining the distance from a given center wavelength where the output emission drops below half of the maximum emission value. The center wavelength of a given LED is preferably maintained within a narrow range to ensure that images collected using different instruments will be of similar quality.

Figure 2:
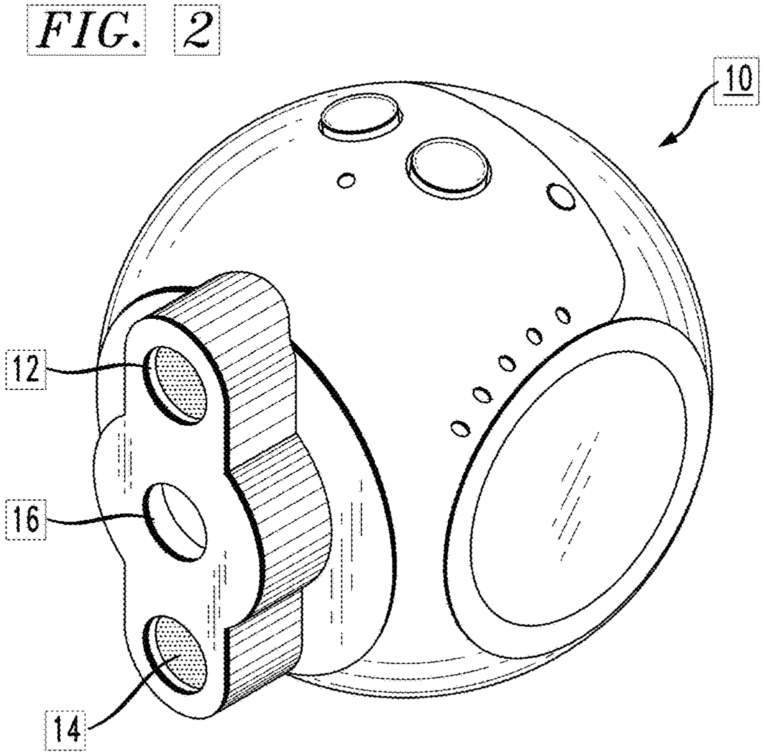
FIG. 2 is a simplified isometric view of an exemplary illumination source formed in accordance with the present invention.

FIG. 2 is a simplified isometric view of an exemplary illumination source 10 formed in accordance with the present invention to be utilized within medical instrumentation such as that illustrated in FIG. 1. In this particular configuration, illumination source 10 is formed to include a pair of opposing apertures 12, 14 through which a narrowband beam from the included LEDs is emitted and directed to an ROI. A central aperture 16 includes a photodetecting arrangement that captures the return light from the ROI. For example, the photodetecting arrangement may take the form of a CCD camera or, preferably, a CMOS detector with appropriate filtering to block stray light outside of the LED wavelengths. As will be discussed in detail below, one or more LEDs may be located at each aperture 12 and 14 (with a white light source in most cases co-located with the LEDs). Additional apertures may be disposed at different locations around the periphery of central aperture 16 to allow for multiple sets of LEDs to be used for narrowband imaging in accordance with the principles of the present invention.

Figure 3:
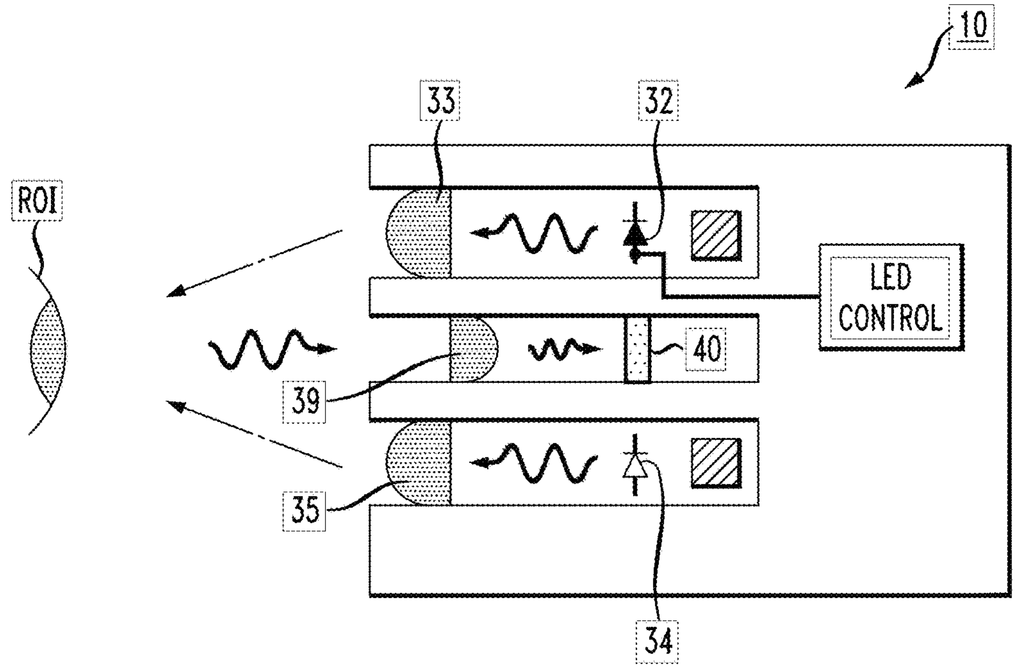
FIG. 3 is a block diagram side view of the illumination source of FIG. 2.

FIG. 3 is a block diagram side view of an exemplary configuration of illumination source 10, in this illustration shown as being used in association with a particular ROI. In this example, a first narrowband LED 32 (operating at a first specifically-defined wavelength $\lambda_1$) is positioned in alignment with aperture 12. When illumination source 10 is part of a colposcopic system, first narrowband LED 32 may be a "green" LED, emitting at a center wavelength $\lambda_1 \approx 540$ nm, with a FWHM value of 30 nm. When illumination source 10 is part of a dermatoscope, first narrowband LED 32 may be a "red" LED, emitting at a center wavelength $\lambda_1 \approx 625$ nm, with a FWHM value of 16 nm. Lensing elements 33 are positioned beyond the output from first LED 32 and used to enable the focusing of the narrowband output from first LED 32 toward the ROI.

Also shown in FIG. 3 is a second narrowband LED 34, operating at a second specifically-defined wavelength and positioned behind aperture 14 of instrumentation 10. When illumination source 10 is part of a colposcope, second narrowband LED 34 may be a "blue" LED, emitting at a center wavelength $\mu_2 \approx 415$ nm, with a FWHM value of 12 nm. When illumination source 10 is part of a dermatoscope, second narrowband LED 34 may be a "yellow" LED, emitting at a center wavelength $\mu_2$580 nm, with a FWHM value of 22 nm. Lensing elements 35 are positioned beyond the output from second LED 34 and used to enable the focusing of the narrowband output from second LED 34 toward the ROI.

A conventional white light source 31 is also shown in FIG. 3, where it is to be understood that the inclusion of white light source 31 is optional, but preferable, since in most cases the medical instrumentation would utilize white light source 31 to illuminate the ROI for a portion of an examination and then energize narrowband LEDs 32, 34 as necessary. Indeed, the turning "on" and "off" of LEDs 32 and 34 is typically under the control of the individual performing the examination, allowing for the capture of high contrast images at specific points in time during the examination procedures. As mentioned above, the activation of the narrowband LEDs may be controlled such that the first-wavelength LEDs 32 are energized for a period of time, and then the second-wavelength LEDs 34 are energized for a different period of time, where the separate activation may provide additional imaging clarity of subsurface elements associated with the different depths penetrated by the different wavelengths.

A photoreceiving element 40 is shown in FIG. 3 as positioned behind central aperture 16, with lensing elements 39 disposed at the entrance of photoreceiving element 40. In accordance with the optical imaging properties of medical instruments, the illumination reflected back towards illumination source 10 from the ROI is captured by photoreceiving element 40 and processed using various types of analysis, well known (and also currently evolving) in the art. Photoreceiving element 40 may comprise, for example, a CCD-based camera or a CMOS detector with appropriate wavelength filtering.

Figure 4:
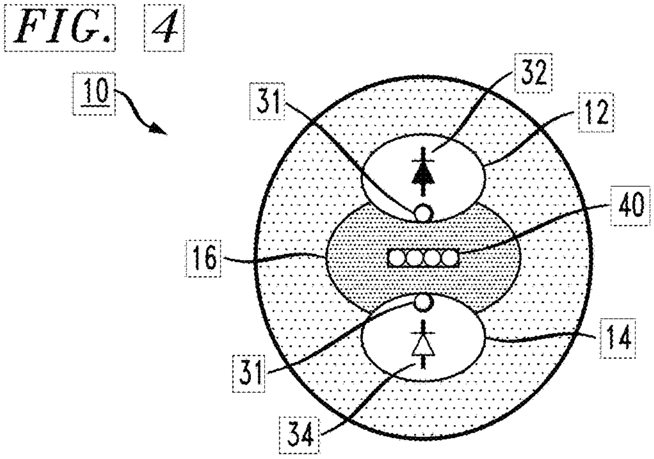
FIG. 4 is a front view of an exemplary arrangement of narrowband LEDs within the inventive illumination source.
Figure 5:
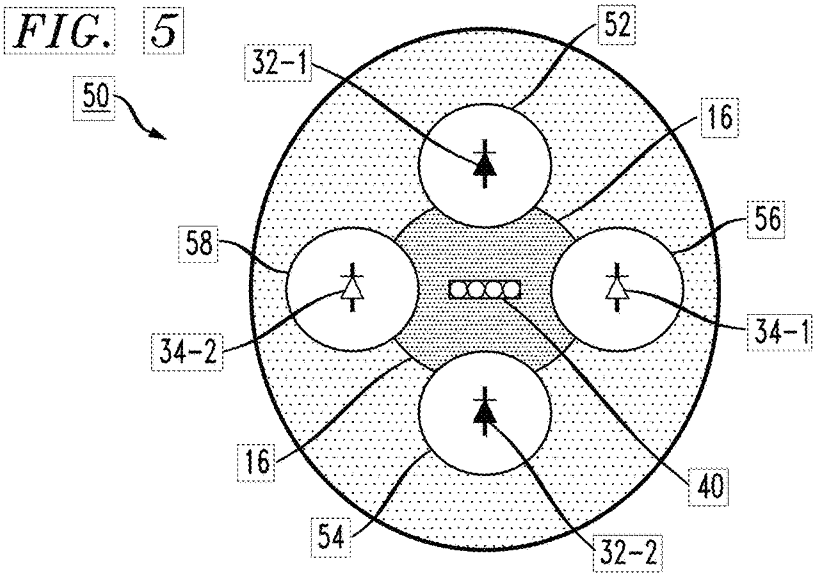
FIG. 5 is a front view of an alternative arrangement of narrowband LEDs within the inventive illumination source.

FIG. 4 is front view of the particular arrangement of LEDs 32 and 34 as shown in FIG. 3. FIG. 5 is a front view of an alternative illumination system 50 utilizing pairs of apertures disposed around central aperture 16. In this particular arrangement a first aperture 52 is positioned at the 0° location around the circular form of illumination system 50, with a second aperture 54 located at the 180° position. A second pair of apertures is disposed orthogonal to apertures 52 and 54, with one aperture 56 located at the 90° position and a remaining aperture 58 located at the 270° position. In this particular configuration, first-wavelength ($\lambda_1$) LEDs 32-1 and 32-2 are disposed behind apertures 52 and 54 (respectively), and second-wavelength ($\lambda_2$) LEDs 34-1 and 34-2 are disposed behind apertures 56 and 58 (respectively).

Figure 6:
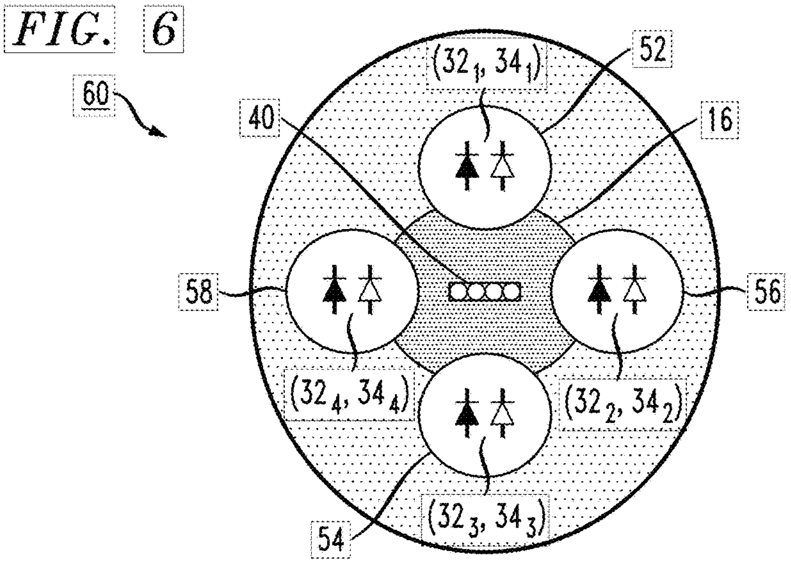
FIG. 6 shown yet another arrangement of narrowband LEDs within an illumination source formed in accordance with the principles of the present invention.

FIG. 6 shows yet a different arrangement. Here, an illumination system 60 maintains the same set of four apertures 52, 54, 56 and 58 as shown in FIG. 5, but in this case is configured to use ($\lambda_1$,$\lambda_2$) pairs of LEDs at each of the four quadrant locations as defined above with respect to the arrangement of FIG. 5. A first pair is identified as (LED $\mathbf{32}_1$, LED $\mathbf{34}_1$); a second pair is identified as (LED $\mathbf{32}_2$, LED $\mathbf{34}_2$); a third pair is identified as (LED $\mathbf{32}_3$, LED $\mathbf{34}_3$); and a fourth pair is identified as (LED $\mathbf{32}_4$, LED $\mathbf{34}_4$).

In each of these embodiments, a specific switching sequence may be used to control the illumination of the separate LEDs, where as mentioned above it is typically the individual performing the examination who controls when the LEDs are turned "on" and "off". However, it is to be understood that a computer-based control of LED sequencing may also be implemented in certain applications.

Figure 7:
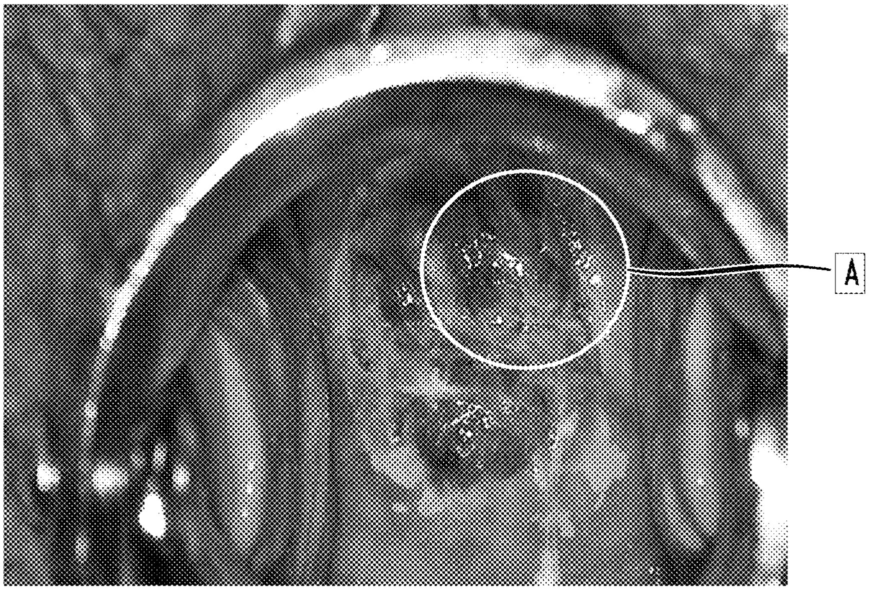
FIG. 7 PRIOR ART
FIG. 7 is a photographic reproduction of a prior art digital image captured with white light.
Figure 8:
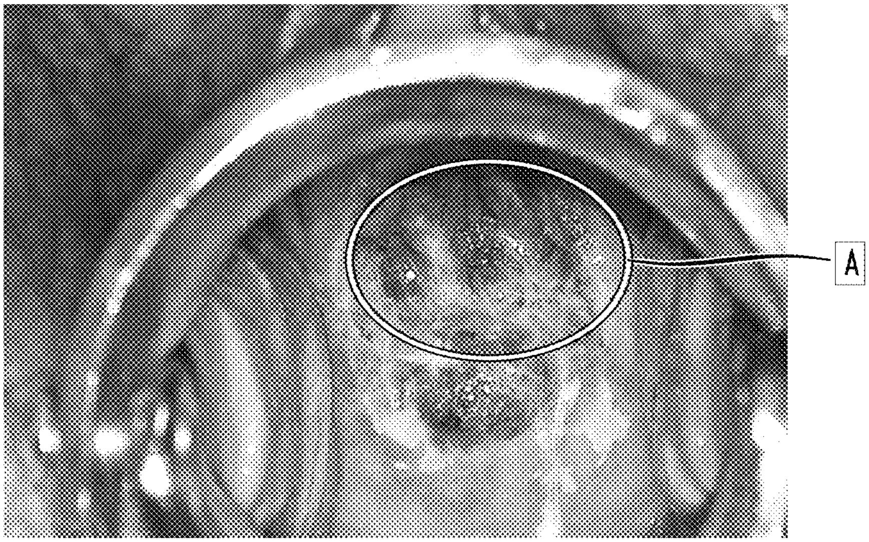
FIG. 8 is a photographic reproduction of the same ROI as shown in FIG. 7, in this case illuminated with narrowband LEDs of a particular wavelength associated with an absorbance peak of the biomolecule(s) present in the ROI.

The ability of the narrowband, wavelength-specific LEDs to provide a higher quality, sharper image of an exemplary ROI is shown by comparing a photographic reproduction of a prior art digital image displayed in FIG. 7 (captured using a traditional white light source) to the digital image displayed in FIG. 8, which was captured using green LEDs as an illumination source in accordance with the teachings of the present invention. The higher contrast result of FIG. 8 is evident in the detailed vasculature of the ROI, particularly in comparative regions A (for example).

It is to be noted that as mentioned above an exemplary LED-based illumination source formed in accordance with the present invention most likely also includes the standard white light illumination source, as still important to capture various other details of the ROI. In an exemplary procedure, for example, a white light illumination source may be used for most of examination, with the narrowband LED-based illumination source activated (as controlled by the clinician, perhaps) during specific periods of time when the vasculature, skin pigmentation, mucosa, or the like, need to be imaged in detail.

In general, the descriptions of the details and embodiments of the narrow band illumination system have been presented for purposes of illustration, but are not intended to be exhaustive or limited to the embodiments disclosed. Many modifications and variations will be apparent to those of ordinary skill in the art without departing from the scope and spirit of the describes embodiments. The terminology used herein was chosen to best explain the principles of the embodiments, the practical application or technical improvement over technologies found in the prior art.

What is claimed is:

1. An illumination source useful in performing digital imaging in conjunction with medical scopic instrumentation, the illumination source comprising:

a photoreceiving element positioned at a centrally-disposed aperture of the illumination source to receive reflected light from an anatomical region of interest (ROI) under study and create a digital image therefrom;

at least one narrowband first-wavelength light emitting diode (LED), positioned at a first emission aperture of the illumination source and specifically formed to emit narrowband light at a first center wavelength $\lambda_1$ associated with a first absorbance peak of the ROI under study, wherein reflected light at the first center wavelength $\lambda_1$ is directed through the centrally-disposed aperture and into the photoreceiving element for creating a first digital image exhibiting a high contrast between normal and abnormal areas in the ROI under study at the first center wavelength $\lambda_1$; and at least one narrowband second-wavelength LED, positioned at a second emission aperture of the illumination source, the second emission aperture disposed in opposition to the first emission aperture such that the first emission aperture and the second emission aperture are positioned at diametrically opposite locations around the centrally-disposed aperture of the illumination source, the at least one narrowband second-wavelength LED specifically formed to emit narrowband light at a second center wavelength $\lambda_2$ associated with a second absorbance peak of the ROI under study, wherein the at least one narrowband first-wavelength LED and the at least one narrowband second-wavelength LED are energized in a switching sequence including energizing the at least one narrowband first-wavelength LED for a first period of time and energizing the at least one narrowband second-wavelength LED for a second period of time different from the first period of time, the energizing of the at least one narrowband second-wavelength LED controlled to illuminate the ROI under study, where reflected light at the second center wavelength $\lambda_2$ is directed through the centrally-disposed aperture and into the photoreceiving element for creating a second digital image exhibiting a high contrast between normal and abnormal areas in the ROI at the second wavelength $\lambda_2$, the at least one narrowband first-wavelength LED and the at least one narrowband second-wavelength LED controllable by an individual performing an examination, allowing for the capture of high contrast images at specific points in time during the examination.

2. The illumination source as defined in claim 1, wherein the illumination source further comprises a white light source for alternative illumination of the ROI the white light source positioned at an emission aperture selected from the group consisting of the first emission aperture, the second emission aperture, and a third emission aperture.

3. The illumination source as defined in claim 1, wherein the photoreceiving element comprises a combination of a CMOS detector and wavelength-dependent filters.

4. The illumination source as defined in claim 1, wherein each narrowband LED exhibits a FWHM of no greater than 30 nm.

5. The illumination source as defined in claim 1, wherein the at least one narrowband first-wavelength LED comprises a plurality of separate first-wavelength LEDs, disposed to illuminate selected areas of the ROI, each first-wavelength LED of the plurality of first-wavelength separate LEDs positioned at a separate one of a plurality of first-wavelength emission apertures positioned around the centrally-disposed aperture of the photoreceiving element.

6. The illumination source as defined in claim 1, wherein the at least one narrowband second-wavelength LED comprises a plurality of separate second-wavelength LEDs, disposed to illuminate selected areas of the ROI, each second-wavelength LED of the plurality of second-wavelength separate LEDs positioned at a separate one of a plurality of second-wavelength emission apertures positioned around the centrally-disposed aperture of the photoreceiving element.

7. The illumination source as defined in claim 1, wherein the at least one narrowband first-wavelength LED and the at least one narrowband second-wavelength LED are disposed at emission apertures proximate to each other in an array at defined locations around a periphery of the photoreceiving element positioned at the centrally-disposed aperture of the illumination source.

8. The illumination source as defined in claim 1, wherein the illumination source is utilized in conjunction with a scopic system for viewing vasculature, the first and second center wavelengths selected to be proximate to absorbance peaks of hemoglobin.

9. The illumination source as defined in claim 8, wherein the at least one narrowband first-wavelength LED operates at a wavelength $\lambda_1 \approx 540$ nm and is referred to as an at least one green LED, and the at least one narrowband second-wavelength LED operates at a wavelength $\lambda_2 \approx 415$ nm and is referred to as an at least one blue LED.

10. The illumination source as defined in claim 9, wherein the at least one green LED comprises a plurality of green LEDs all operating at a wavelength $\lambda_1 \approx 540$ nm.

11. The illumination source as defined in claim 9, wherein the at least one blue LED comprises a plurality of blue LEDs all operating at a wavelength $\lambda_2 \approx 415$ nm.

12. The illumination source as defined in claim 8, wherein the at least one green LED comprises a plurality of green LEDs all operating at a wavelength $\lambda_1 \approx 540$ nm, and the at least one blue LED comprises a plurality of blue LEDs all operating at a wavelength $\lambda_2 \approx 415$ nm.

13. The illumination source as defined in claim 1, wherein the illumination source is utilized in conjunction with a dermatoscope, the first and second center wavelengths selected to be proximate to absorbance peaks of skin pigments.

14. The illumination source as defined in claim 13, wherein the at least one narrowband first-wavelength LED operates at a wavelength $\lambda_1 \approx 625$ nm and is referred to as an at least one red LED, and the at least one narrowband second-wavelength LED operates at a wavelength $\lambda_2 \approx 580$ nm and is referred to as an at least one yellow LED.

15. The illumination source as defined in claim 14, wherein the at least one red LED comprises a plurality of red LEDs all operating at a wavelength $\lambda_1 \approx 625$ nm.

16. The illumination source as defined in claim 14, wherein the at least one yellow LED comprises a plurality of yellow LEDs all operating at a wavelength $\lambda_2 \approx 580$ nm.

17. The illumination source as defined in claim 14, wherein the at least one red LED comprises a plurality of red LEDs all operating at a wavelength $\lambda_1 \approx 625$ nm, and the at least one yellow LED comprises a plurality of yellow LEDs all operating at a wavelength $\lambda_2 \approx 580$ nm.

* * * * *